(12) United States Patent
Skelton

(10) Patent No.: US 10,753,626 B2
(45) Date of Patent: Aug. 25, 2020

(54) AIR TREATMENT UNIT

(71) Applicant: PetAirapy LLC, St. Charles, IL (US)

(72) Inventor: David Skelton, Bartlett, TN (US)

(73) Assignee: PETAIRAPY LLC, St. Charles, IL (US)

( * ) Notice: Subject to any disclaimer, the term of this patent is extended or adjusted under 35 U.S.C. 154(b) by 284 days.

(21) Appl. No.: 15/871,719

(22) Filed: Jan. 15, 2018

(65) Prior Publication Data
US 2019/0219284 A1    Jul. 18, 2019

(51) Int. Cl.
*F24F 3/16*    (2006.01)
*A61L 9/20*    (2006.01)

(52) U.S. Cl.
CPC    *F24F 3/16* (2013.01); *A61L 9/20* (2013.01); *A61L 2209/12* (2013.01); *A61L 2209/134* (2013.01); *A61L 2209/16* (2013.01); *F24F 2003/1667* (2013.01)

(58) Field of Classification Search
CPC ..................................... A61L 9/20; F24F 3/16
USPC ........................................................ 422/24
See application file for complete search history.

(56) References Cited

U.S. PATENT DOCUMENTS

| | | | | |
|---|---|---|---|---|
| 5,225,167 A | * | 7/1993 | Wetzel | A61L 9/20 96/224 |
| 6,855,295 B2 | * | 2/2005 | Kulp | F24F 3/16 422/121 |
| 8,734,724 B2 | * | 5/2014 | Engelhard | A61L 9/205 422/121 |

* cited by examiner

*Primary Examiner* — Kevin Joyner
(74) *Attorney, Agent, or Firm* — Wood, Phillips, Katz, Clark & Mortimer

(57) ABSTRACT

An air treatment unit has: a) a frame; b) a source of UV light that is configured to disinfect air, the frame configured to be mounted in an operative position within a space in which air is to be disinfected, the frame configured to allow air from a duct through which air is forced into the space to be directed in a manner that expelled air from the duct is caused to be disinfected by UV light from the source of UV light with the frame and source of UV light each operatively positioned; and c) an air moving assembly that causes air within the space to be directed into a volume that has UV light rays from the source of UV light therein capable of disinfecting air.

18 Claims, 6 Drawing Sheets

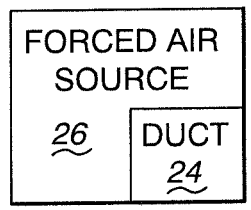
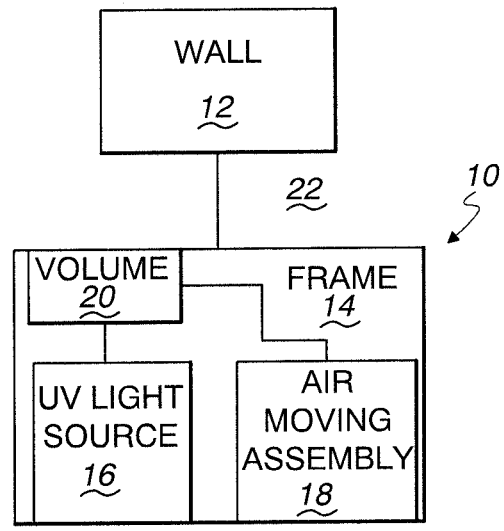
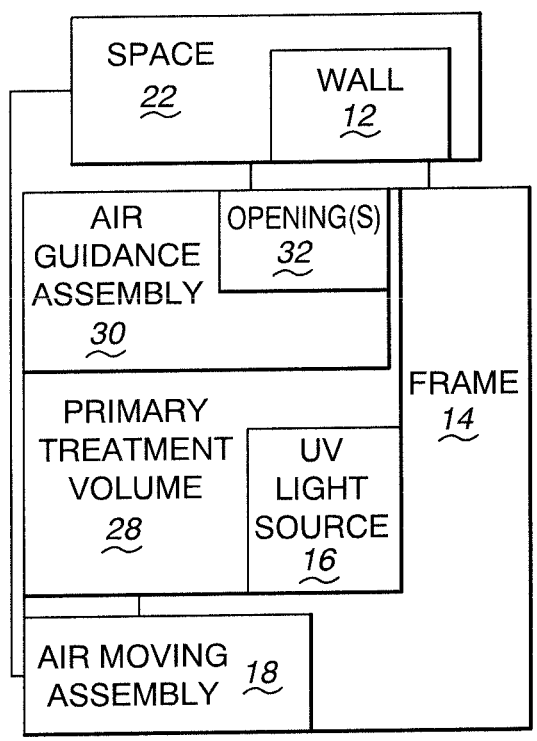
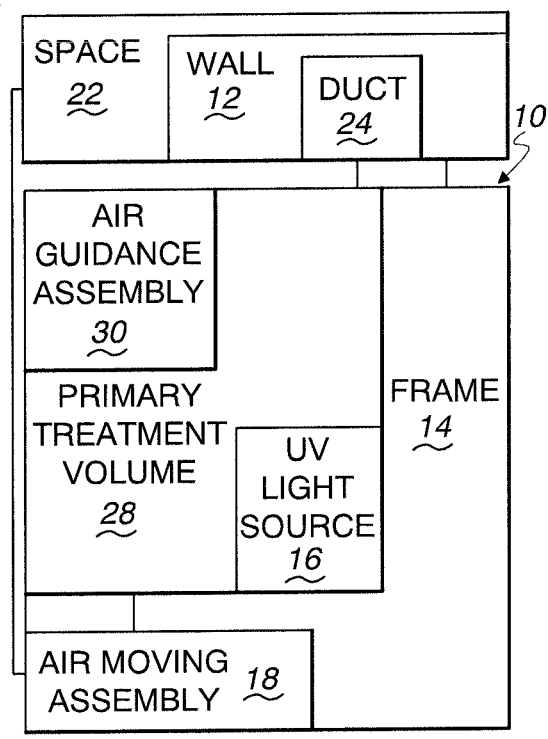

AIR TREATMENT UNIT

BACKGROUND OF THE INVENTION

Field of the Invention

This invention relates to environmental air treatment and, more particularly, to a treatment unit that causes air to be disinfected by being exposed to UV light.

Background Art

UV-C, also known as "germicidalultraviolet" light, is known to deactivate molds, spores, and germs contained in tiny airborne droplet nuclei that transmit diseases such as measles, tuberculosis, and influenza from animal or human to animal or human. With significant intensity, UV-C can penetrate the cell wall of a microorganism and destroy it, but cannot penetrate the outer layer of a pet's or a human's skin or the cornea of the eye.

A multitude of systems have been devised to treat environmental air in which humans and pets reside. UV-C fixtures are currently available for disinfecting air as it is mechanically forced through ventilation ductwork and proximate to germicidal lamps, commonly referenced as "in-duct" UV-C fixtures. The radiation from the UV-C fixture neutralizes pathogens that would otherwise contaminate air as they are mixed and circulated/recirculated via one or more ventilation air ducts. A system fan moves contaminated air through ductwork, as an incident of which airborne pathogens are forced to pass proximate to and through a germicidal energy field generated by one or more UV-C lamps located in the air path/supply vent.

Specific pathogens can be targeted by applying published lethal UV-C energy doses to the air as it passes through the ductwork and the supply vent that distributes air to a space. These in-duct UV-C fixtures are commonly mounted in one of three locations: a) within the ductwork; b) in the air plenum proximate to HVAC cooling/heating coils; and/or c) at or inside the supply vent as the air exits the duct and is dispersed through a space.

In-duct air disinfection is achieved when air is mechanically forced through a ventilation system, past one or more UV-C lamps, and into a space through a supply vent.

Another form of system uses UV-C fixtures to disinfect air that naturally or mechanically rises upwardly within a room at a height above occupants' heads. These fixtures are commonly mounted to upper walls or ceilings and project germicidal light outwardly in a generally horizontal path. This "upper-air" disinfection technology exploits the natural, passive movement of air within a space through the physical law of convection—hot air rising and cool air falling.

Any source of heat in a space accelerates convection rates. Upper-air fixtures employ UV-C lamps to generate light energy that is broadcast into a room at a specific height, typically at seven feet or more to be overhead standing room occupants. Light baffles or louvers cause the germicidal energy to be dispersed into the space in a tightly defined, narrow, energy band, known as an airborne pathogen "kill zone" of UV-C light energy.

In spaces with taller ceilings—typically 9+ feet—open fixtures can flood the upper part of the room while a shelf or lip prevent germicidal light from dispersing into the lower, occupied space in the room. These upper-air fixtures are often referenced as TB, or tuberculosis, lights, given their common use in countries with high occurrences of tuberculosis and other respiratory diseases. Fans may be used to accelerate and assist in increased air turn rates to increase the movement of contaminated air through the germicidal energy zone. Air disinfection is achieved only when air is moved, either mechanically or naturally, through the germicidal disinfection field created in the upper room space.

It is also known to disinfect air by forcing air through dedicated, defined disinfection chambers. These systems may be wall-mounted, hung from ceilings, or installed in conjunction with another type of system. This category of system pushes or pulls contaminated air through a fixed chamber, proximate to a UV-C germicidal lamp, and then causes the treated air to be distributed into a space. These systems are similar in structure and operate on the same basic principles as conventional floor air cleaners. Air disinfection is achieved only when air is mechanically pulled or pushed through the enclosed system, past a UV-C lamp, and then forced into a space.

Air destratification is practiced to be complementary to one or more of the above systems. Because cool air falls and warm air rises, stagnant air becomes stratified in confined spaces with warm air accumulating near the ceiling and cold air near the floor. Destratification technology uses one or more fans to accelerate the natural convection movement of contaminated air through a UV-C "kill zone". If there is little or no heat source to generate sufficient convection currents, and no mechanical movement of stagnant air in a room, one or more fans may be used to move warm air from near the upper part of a room toward the floor, and conversely move cool air near the floor to the upper part of a room. The objective of the destratification is to eliminate hot/cold spots and create an environmental average of hot/cold air temperatures and to move air through the UV-C "kill zone". Existing paddle-type ceiling fans are commonly used for purposes of destratification and air mixing to improve the efficiency of air disinfection technology.

The industry continues to seek improved systems that will more effectively deactivate molds, spores, and germs in spaces occupied by humans and pets, without causing user inconvenience or presenting any health hazard to humans, pets, or other animals.

SUMMARY OF THE INVENTION

In one form, the invention is directed to an air treatment unit has: a frame; a source of UV light that is configured to disinfect air; and an air moving assembly that causes air within a space to be directed into a volume that has UV rays, from the source of UV light, therein capable of disinfecting air. The frame is configured to be mounted in an operative position within a space in which air is to be disinfected. The frame is configured to allow air from a duct, through which air is forced into the space, to be directed in a manner that expelled air from the duct is caused to be disinfected by UV light from the source of UV light with the frame and source of UV light each operatively positioned.

In one form, the air treatment unit is configured to define a primary treatment volume. The primary treatment volume is bounded by a bottom wall making up a part of the frame.

In one form, the frame further includes an air guidance assembly that extends around the primary treatment volume.

In one form, the air guidance assembly is configured to define at least one elongate opening through which air can be communicated between the primary treatment volume and a region of the space outside of the primary treatment volume with the frame operatively positioned.

In one form, the air treatment unit is configured to define a primary treatment volume through which a vertically extending axis extends with the frame operatively positioned. The frame further includes an air guidance assembly that extends around the vertically extending axis and is configured to define radial communication paths for air between the primary treatment volume and a region of the space outside of the primary treatment volume substantially fully around the vertically extending axis.

In one form, the air guidance assembly is configured to define at least one elongate opening through which air can communicate between the primary treatment volume and the region of the space outside of the primary treatment volume.

In one form, the air guidance assembly has a plurality of spaced slats. The at least one elongate opening is in the form of a louver between at least first and second of the spaced slats.

In one form, the air moving assembly has a fan on the frame that is configured to draw air in the space upwardly into the primary treatment volume with the frame operatively positioned.

In one form, a vertically extending axis extends through the primary treatment volume with the frame operatively positioned. The source of UV light consists of a plurality of lamps at spaced angular positions around the vertically extending axis.

In one form, with the frame operatively positioned, the fan causes air within the space to move in a substantially vertically directed path into the primary treatment volume.

In one form, the vertically extending axis extends through the vertically directed path in which air is moved by the fan.

In one form, the frame is symmetric on diametrically opposite sides of a reference plane containing the vertically extending axis.

In one form, the frame is configured to be flush mounted to a downwardly facing ceiling surface with the frame operatively positioned.

In one form, the frame has at least one support edge configured to engage a ceiling grid T-bar system so as to thereby maintain the frame in the operative position.

In one form, the air treatment unit further includes a suspension assembly configured to maintain the frame spaced from a downwardly facing ceiling surface with the frame operatively positioned.

In one form, the air treatment unit is provided in combination with a support for the frame relative to which the frame is maintained in the operative position, and further in combination with a duct through which air is forced into the space. The frame is configured to define a primary treatment volume. The duct is configured to cause air expelled from the duct to be moved directly into the primary treatment volume.

In one form, the air from the duct moves in a downwardly directed path into the primary treatment volume. The air moving assembly has a fan configured to draw air in the space in an upwardly directed path into the primary treatment volume.

In one form, the upwardly and downwardly directed paths at least partially coincide so that air in the upwardly and downwardly directed paths is caused to mix. The frame has at least one elongate opening situated so that a volume of the mixed air is diverted in a non-vertical direction through the at least one elongate opening from the primary treatment volume into a region of the space outside of the primary treatment volume.

In one form, the primary treatment volume has a vertically extending central axis with the frame operatively positioned. The central axis extends through and generally parallel to the upwardly and downwardly directed paths. The source of UV light consists of a plurality of lamps spaced from the central axis and from each other around the central axis.

In one form, the plurality of UV lamps are arranged around the central axis to produce a substantially uniform density of UV light rays within the primary treatment volume.

BRIEF DESCRIPTION OF THE DRAWINGS

FIG. 1 is a schematic representation of one form of air treatment unit, according to the invention;

FIG. 2 is a schematic representation of a more specific form of air treatment unit as in FIG. 1;

FIG. 3 is a schematic representation of an alternative form of air treatment unit as shown generically in FIG. 1;

DETAILED DESCRIPTION OF THE PREFERRED EMBODIMENT

Figure 4:
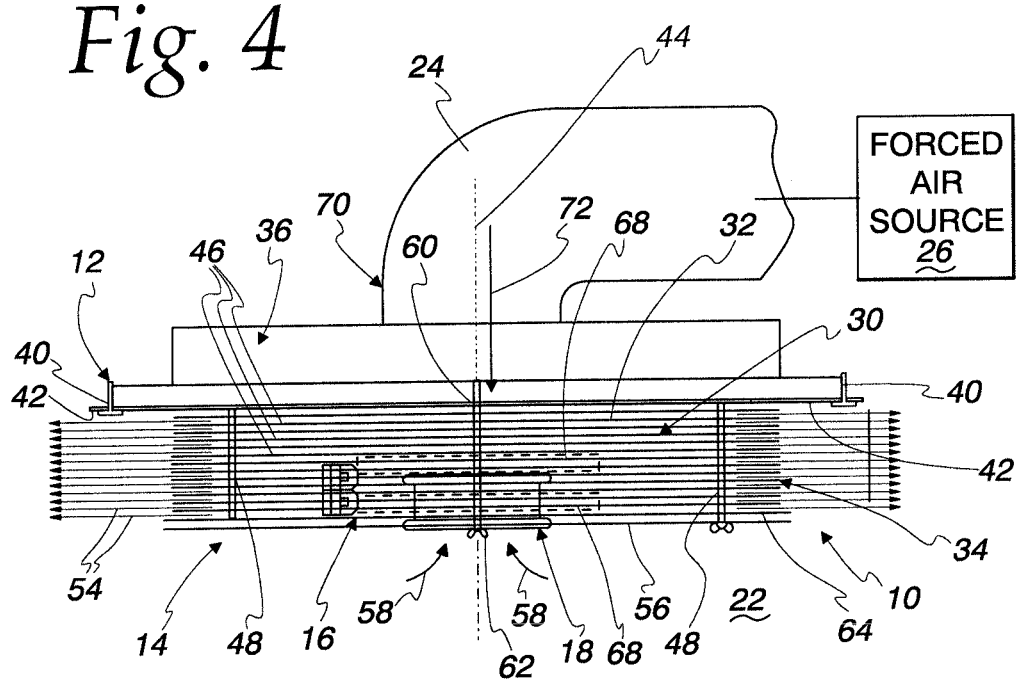
FIG. 4 is a side elevation view of one specific form of the inventive air treatment unit, as shown generically in FIG. 1, and in an operative state with respect to an existing duct which introduces treated air into a space.

In FIG. 1, an air treatment unit, according to the present invention, is shown in schematic form at 10. The air treatment unit 10 is preferably configured to be attached to a wall 12, which is most preferably a ceiling wall, but could be a peripheral side wall surrounding an occupiable space.

The air treatment system 10 has a frame 14 that is mounted to the wall 12. The frame 14 supports a light source 16, characterized herein as a "UV light source", which is intended to encompass all different forms of light known to those skilled in the art capable of deactivating molds, spores, germs, etc., that are entrained in air, to thereby effect disinfecting of that air.

The frame 14 further supports an air moving assembly 18 that causes air within a space to be directed into a frame volume 20 that has UV rays from the source 16 therein capable of disinfecting air.

By mounting the frame 14 to the wall 12, the frame 14 is maintained in an operative position within a space 22 in which air is to be disinfected. The air moving assembly 18 causes room air to be directed into the volume 20, wherein it is treated by the UV light source and thereafter reintroduced to the space 22.

The frame 14 is also configured to allow air expelled from a duct 24 on a forced air source 26 to be directed into the volume 20 for treatment by the UV rays from the light source 16.

FIGS. 2 and 3 show alternative setups for the air treatment unit 10 within the space 22. In these Figures, additional details of the air treatment unit 10 are also shown.

In FIG. 2, a primary treatment volume 28 is shown on the frame 14 with direct exposure to the operatively positioned UV light source 16. In the primary treatment volume 28 there is an active germicidal energy field. An air guidance assembly 30 has at least one opening 32, preferably with an elongate configuration, through which air from the primary treatment volume 28 passes to be distributed to the space 22 with the frame 14 operatively positioned on the wall 12. Preferably, the opening(s) 32 has/have a louver arrangement wherein UV light from the source 16 creates a kill zone within the openings 32 wherein the air is further disinfected before dispersing into the space 22.

Immediately outside of the frame 14 there exists a passive external germicidal energy field that treats the room air. That is, UV rays are directed through the louvers/openings 32 to the region immediately outside of the frame 14 and have sufficient intensity in this region to effect a significant level of passive treatment.

The air moving assembly 18 forces air from the space 22 into the primary treatment volume 28 to avoid room air stagnation.

The system 10 in FIG. 3 has the same basic construction for the frame 14, and similar components thereon, including the UV light source 16, the primary treatment volume 28, the air guidance assembly 30, and the air moving assembly 18.

Additionally, the frame 14 is configured so that the aforementioned duct 24 on the wall 12 forces air, typically conditioned through an HVAC system, directly into the primary treatment volume 28.

When the forced air source 26 and air moving assembly 18 are operating at the same time, air from the duct 24 and air moving assembly 18 is caused to mix within the primary treatment volume 28, wherein it is treated by the UV radiation from the source 16.

The schematic representation of components in FIGS. 1-3 is intended to encompass the components, as shown in specific embodiments described hereinbelow, and virtually an unlimited number of variations of those components and their interaction. The preferred embodiments described herein are exemplary in nature only and represent specific forms of the invention as generically defined in FIGS. 1-3.

Figure 5:
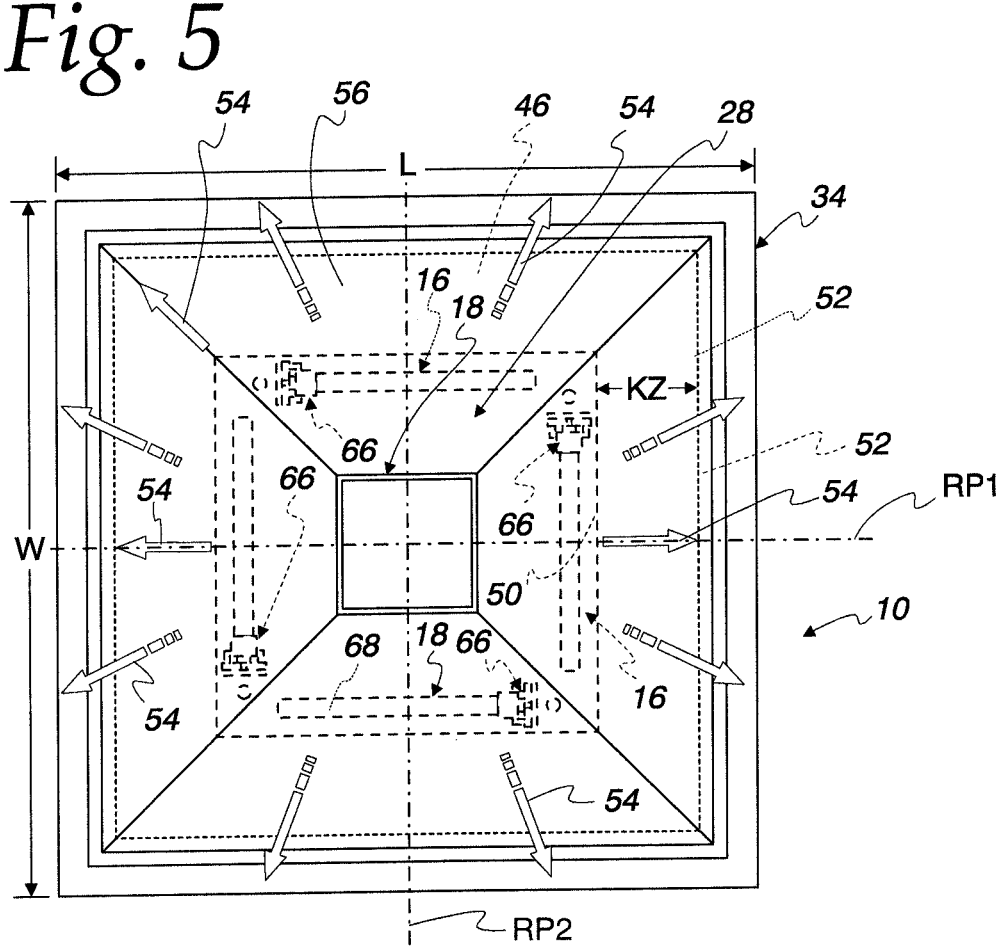
FIG. 5 is a bottom view of the air treatment unit in FIG. 4.

One exemplary form of the air treatment unit 10 is shown in FIGS. 4 and 5. The frame 14 has a main frame portion 34 and a subframe portion 36.

The subframe portion 34 is used to effect mounting of the frame 14 to the wall 12. In this embodiment, the subframe portion 36 has a mounting portion 38 that spans between, and is supported upon, T-bar components 40 on a ceiling grid T-bar system so that with the frame 14 in the operative position of FIG. 4, the main frame portion 34 depends from the downwardly facing ceiling surface 42.

In this embodiment, the length L and width W of the frame 14 are the same, with one preferred length and width dimension being 24 inches.

The components shown in FIGS. 4 and 5 are shown substantially to scale based upon the length and width L, W each being twenty four inches. The primary treatment volume 28 has a square shape as viewed along a vertical central axis 44. The air guidance assembly 30 extends around and effectively frames the primary treatment volume 28, as viewed from below in FIG. 5.

The air guidance assembly 30 consists of a series of slats 46, each with a square frame shape. The slats 46 are mounted through a plurality of rods 48 depending from the subframe portion 36. The slats 46 are flat and are mounted in a close vertically spaced relationship to define louvers corresponding to the aforementioned elongate opening(s) 32. The louvers/openings 32 define the aforementioned kill zone as air distributes radially outwardly relative the central axis 44 from the primary treatment volume 28 between the inner edges 50 of the slats 46 and the perimeter outer edges 52 thereof. This kill zone region is identified by the width dimension KZ in FIG. 5. Air is forced to travel within the louvers/openings 32 over the distance KZ and, in its overall path within the treatment energy field, between the primary treatment volume 28 and a region of the space 22 outside of the primary treatment volume.

With this arrangement, air within the primary treatment volume 28 distributes through the louvers/openings 32 radially in a pattern substantially 360° around the central axis 44. This flow pattern is identified generally by the arrows 54.

Air flow into the primary treatment volume 28 in a downward direction is blocked by a bottom wall 56 on the frame 14, which defines the lower boundary of the primary treatment volume 28.

The bottom wall 56 supports the air moving assembly 18, which is a conventional-type fan that draws air from the space 22 generally axially upwardly into the primary treatment volume 28, as indicated by the arrows 58.

The bottom wall 56 and air moving assembly 18 can be constructed to move as one piece and are supported together on hanging rods 60 depending from the subframe portion 36. A wingnut 62 is shown for securing the bottom wall 56 on the bottom of one of the hanger rods 60 in the operative position of FIG. 4, wherein the bottom wall 56 blocks the primary treatment volume 28 and provides a decorative cover for the unit 10, including over the downwardly facing surface 64 of the bottommost slat 46. With this arrangement, by removing the wingnuts 62, the bottom wall 56 and air moving assembly 18 thereon can be lowered to better access the air moving assembly 18 and to also access the primary treatment volume 28 and the plurality of lamps 66, together making up the UV light source 16.

In this embodiment, four lamps 66 are mounted to the frame 14 at equal distances from the central axis 44. The lamps 66 are arranged at regular angular intervals around the axis 44. In this embodiment, the lamps 66 cooperatively produce a square shape that is complementary to the shape of the primary treatment volume 28, as viewed along the axis 44. As depicted, each lamp 66 includes a pair of bulbs 68. Precise construction of the lamps 66 and their placement may vary considerably. One skilled in the art could readily come up with different arrangements to maximize exposure of air to the UV radiation generated by the lamps 66 within the primary treatment volume 28, the kill zone region in the louvers/openings 32, and in the passive treatment region outside of the frame 14.

The ability to separate the bottom wall 56 facilitates placement and maintenance of the lamps 66, as to change bulbs 68, and also permits cleaning of the slats 46 which may accumulate dust over time which contrasts with the preferred black coloration of the exposed slat surfaces.

The subframe portion 36 is constructed so that the duct 24 can be connected thereto or positioned in relationship therewith, so that a discharge region 70 expels air from the forced air source 26 preferably downwardly, as indicated by the arrow 72, directly into the primary treatment volume 28. The forced air source 26 may be any type of structure that produces pressurized air and is typically one that delivers heated or cooled air under pressure to and through the duct 24 into the space 22.

While not required, in the depicted embodiment, the central axis 44 coincides with the downwardly moving path of air from the duct 24 and the upwardly moving path of air generated by the air moving assembly/fan 18. As depicted, the axis 44 is at the center of both paths, which are substantially parallel to each other.

The upwardly and downwardly directed air paths at least partially coincide so that air in the separate paths is caused to mix within the primary treatment volume 28 and is thereafter diverted in a non-vertical direction through the louvers/openings 32 into a region of the space outside of the primary treatment volume 28.

Commonly, the air moving assembly 18 will be running constantly with the air treatment unit 10 in an "on" state. Thus, air is continuously drawn from the space 22 upwardly into the primary treatment volume 28, exposed to the radiation field generated by the UV light source 16 therein, and further treated in the kill zone within the louvers/openings 32 from where it is dispersed back into the space 22 and there passively treated in a region immediately outside of the frame 14.

When the forced air source 26 is operated, the incoming flow of air from the duct 24 becomes exposed to the radiation within the primary treatment volume 28 as it is mixed with the flow generated by the air moving assembly/fan 18. Thus, the incoming air is disinfected by the air treatment unit 10 as it is introduced into the space 22. The pressure from the duct air causes a higher pressure distribution of air radially outwardly from the air treatment unit 10 relative to the axis 44.

It should be understood that the invention also contemplates a more passive introduction of duct air as contemplated in the FIG. 2 embodiment.

Further, the description of the structure in FIGS. 4 and 5, and others hereinbelow, relative to a ceiling mount is intended to be exemplary as one particular operative position for the air treatment unit 10. The air treatment unit 10 could be mounted other than on a ceiling. Thus, the reference to vertical and horizontal should not be limited to a ceiling mount, and these references are arbitrary in the event that the air treatment unit is mounted in another orientation.

Also, while not necessary, for purposes of uniformity of air treatment, the frame 24 is symmetrical on diametrically opposite sides of a reference plane containing the vertically extending axis 44. In this embodiment, the frame is symmetrical about orthogonal reference planes RP1, RP2 extending through the central axis 44.

Some variations in the air treatment unit 10, as described above, will now be described. Again, it is should be emphasized that these different versions are intended only to be exemplary in nature, showing other potential operating features and mounting options.

Figure 6:
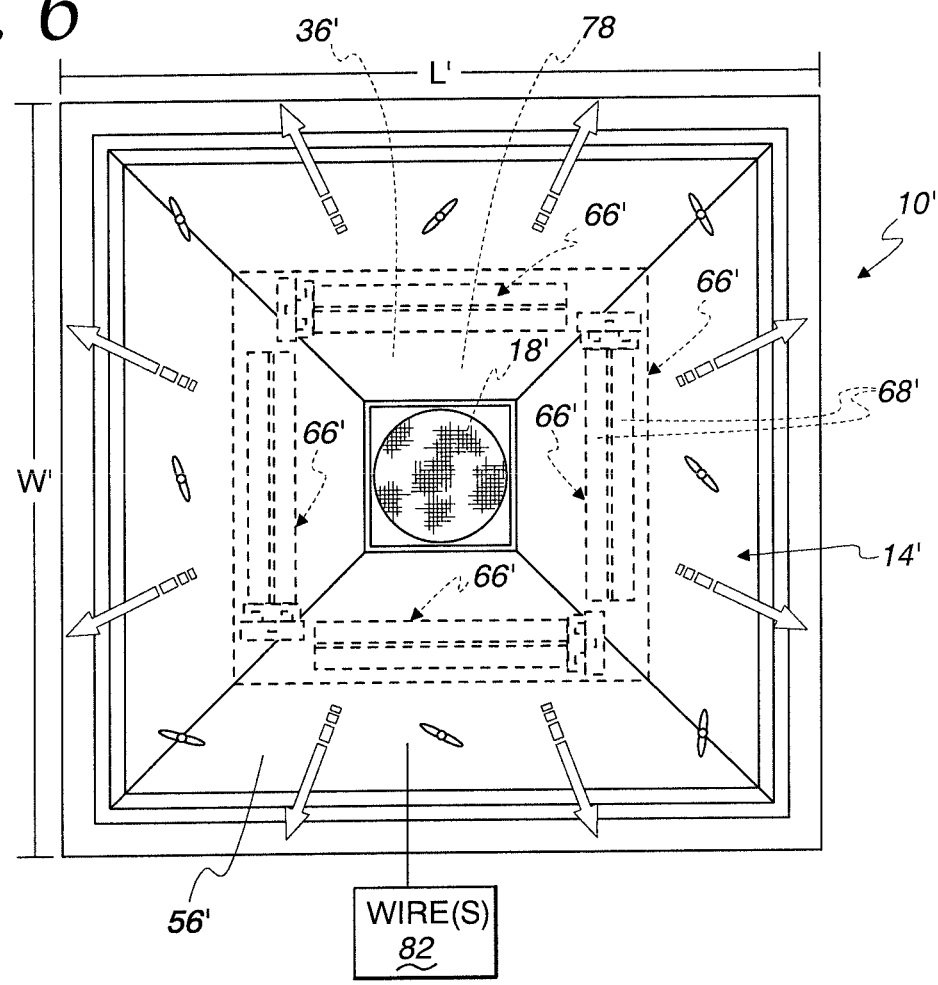
FIG. 6 is a view as in FIG. 5 of a modified form of air treatment unit, according to the invention.
Figure 7:
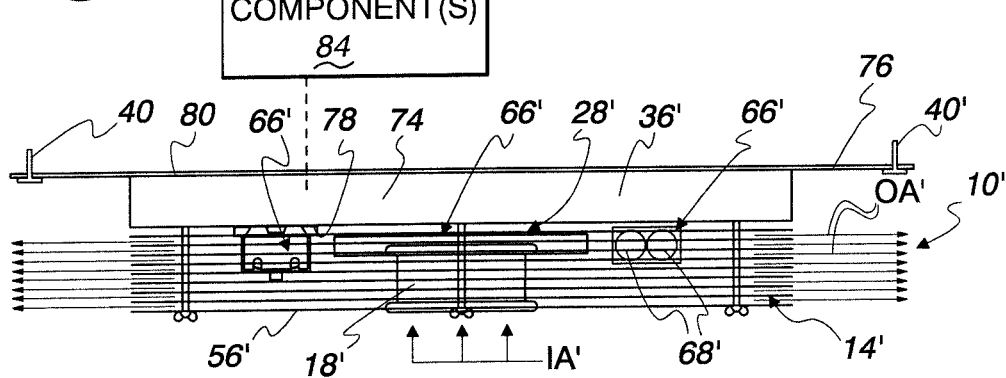
FIG. 7 is a side elevation view of the air treatment unit in FIG. 6.

In FIGS. 6 and 7, a treatment unit 10' is shown that is similar to the treatment unit 10 with a primary difference being that the subframe portion 36' is modified from the subframe 36. In this embodiment, the subframe portion 36' has a squared housing 74 with an upper, outwardly projecting flange 76 that is supported on T-bar components 40 on a drop ceiling to maintain the frame 14' in its operative position.

The lamps 66' are mounted on a downwardly facing surface 78 on the housing 74 within a primary treatment volume 28'. The lamps 66' are arranged so that the bulbs 68' are in side-by-side relationship as opposed to in vertically spaced relationship, as shown for the bulbs 68 in FIGS. 4 and 5.

An air moving assembly/fan 18' is mounted on a bottom wall 56' to draw in room air in a direction of the arrows IA', with treated air directed into the room space in a pattern indicated by the arrows OA'.

The air treatment unit 10' otherwise generally functions in the same manner as the air treatment unit 10, as described above.

The top wall 80 of the subframe portion 36' may have an opening as large as a discharge opening on the duct 24, or may simply allow passage of one or more wires 82 associated with electrical components 84 on the frame 14' and required to operate the lamps 66', air moving assembly/fan 18', and any other electrical components.

Figure 8:
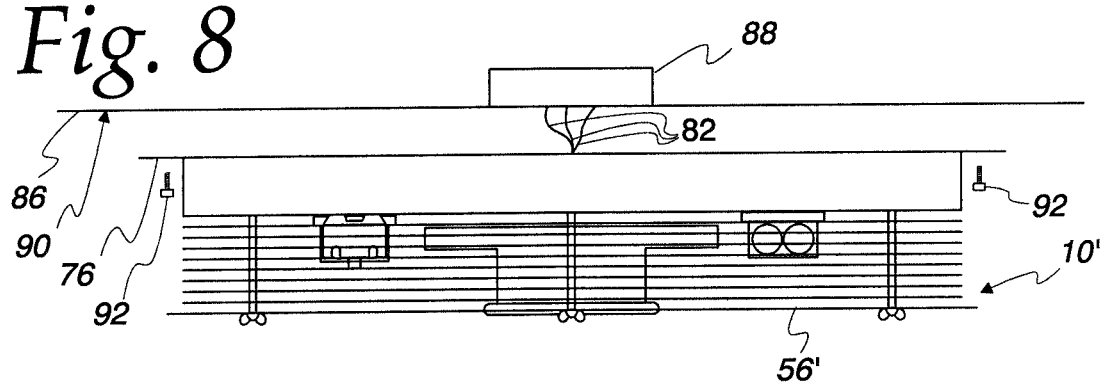
FIG. 8 is a side elevation view as in FIG. 7 with the air treatment unit lowered with respect to a mounting wall.
Figure 9:
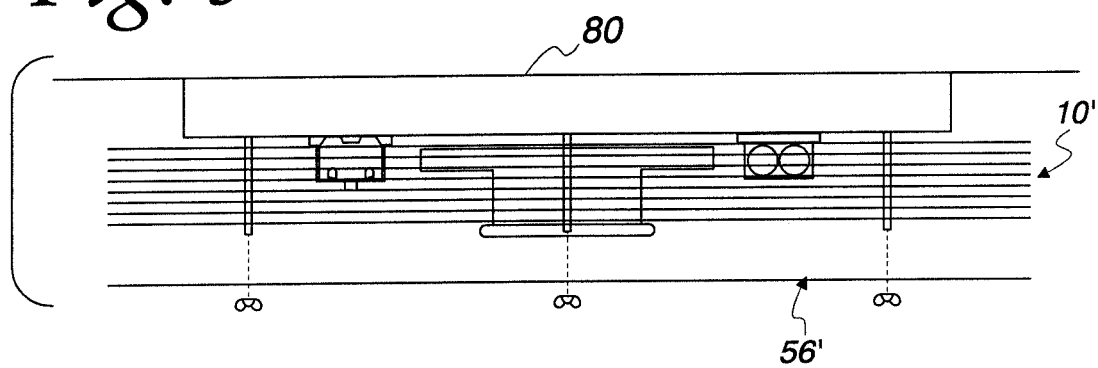
FIG. 9 is a view as in FIG. 8 with a bottom wall on the air treatment unit separated.
Figure 10:
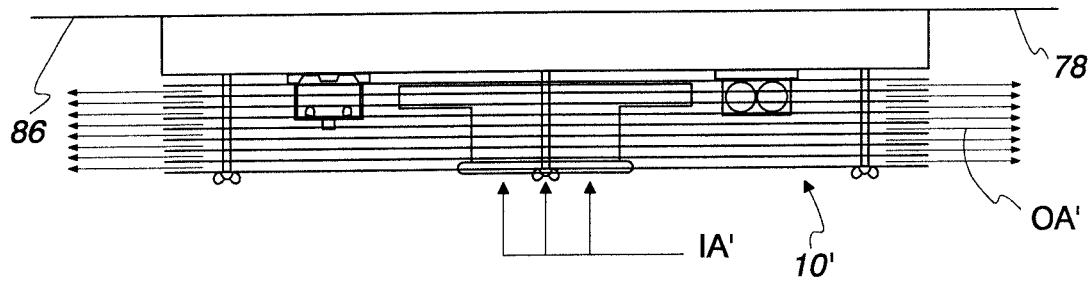
FIG. 10 is a view as in FIG. 9 with the air treatment unit in an operative state.

A like, or identical, unit 10' can be flush mounted to a surface 86, as shown in FIGS. 8-10. Mounting may be effected with the bottom wall 56' separated, as shown in FIG. 9, to facilitate access to a top wall 80 through the primary treatment volume 28'. This also facilitates the connection of the wires 82 within a junction box 88 on the wall 90 defining the mounting surface 86. Conventional fasteners 92 can be used to secure the flange 76 against the surface 86 to maintain the unit 10' in its operative position, as shown in FIG. 10. Air flow pattern is identical to that shown in FIG. 7, as indicated by the arrows IA', OA'.

In FIGS. 11-14, a modified form of air treatment unit is shown at 10", including sequence drawings showing how the same is installed with respect to ceiling T-bar components 40 on a drop ceiling.

The air treatment unit 10" is substantially the same as the air treatment unit 10', with the main difference being that the air moving assembly/fan 18" is mounted to depend from a downwardly facing surface 94 on the bottom wall 56".

Figure 11:
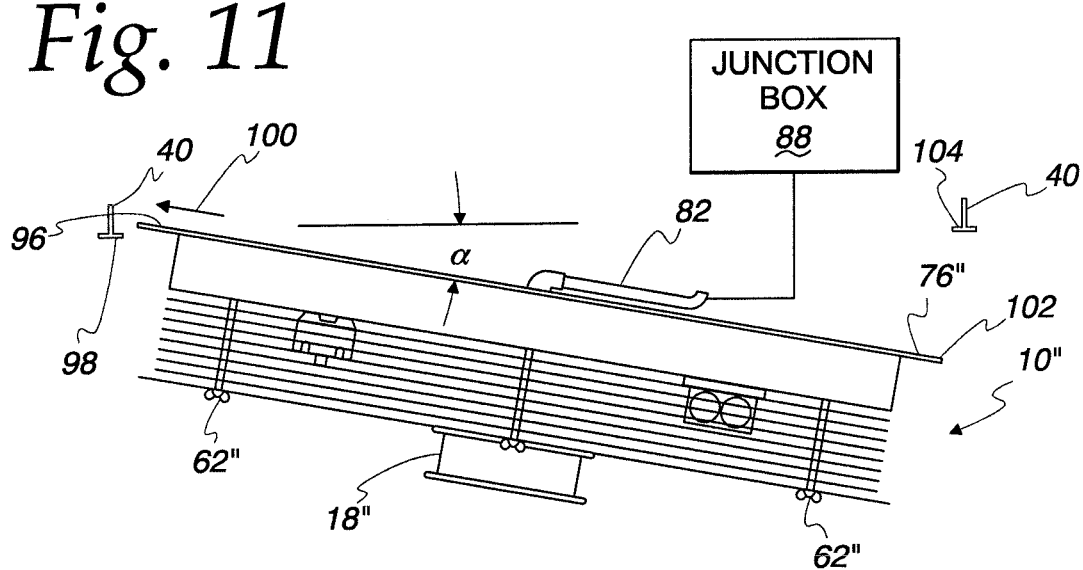
FIG. 11 is a side elevation view of a further modified form of air treatment unit, according to the invention, in a preassembly position with respect to T-bar components on a drop ceiling.
Figure 12:
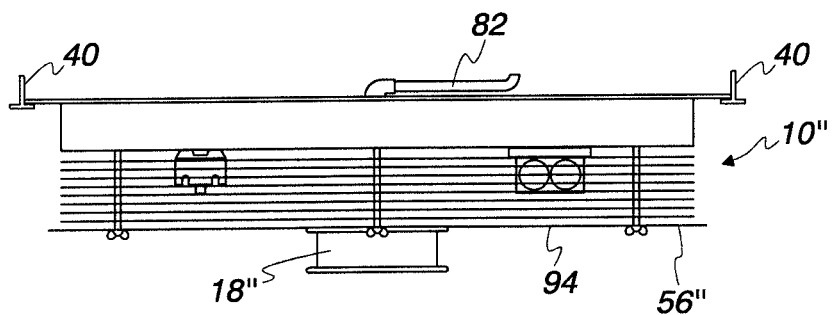
FIG. 12 is a view as in FIG. 11 with the air treatment unit in an operative state.
Figure 14:
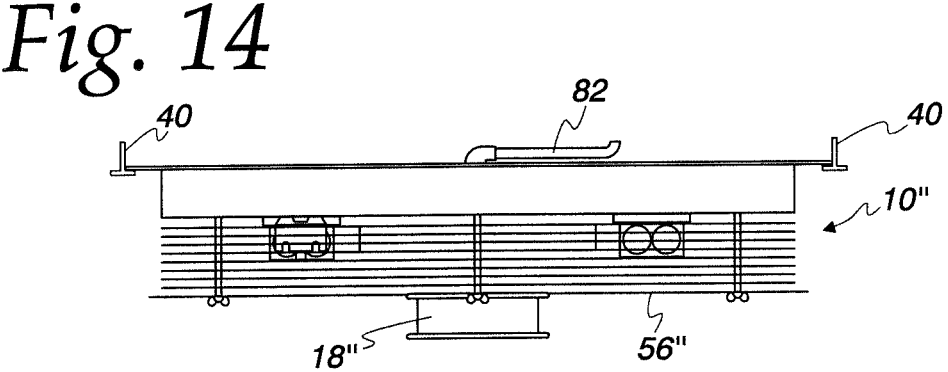
FIG. 14 is a view as in FIG. 13 with the wall reattached.

FIG. 11 also shows the initial step for placing the air treatment unit 10" in its operative position of FIG. 14. As shown, the entire air treatment unit is placed at an angle α to horizontal. In this orientation, a leading end 96 of the flange 76" is situated so that it can be directed over a horizontal leg 98 on the T-bar component 40. By then being shifted in the direction of the arrow 100, the trailing end 102 of the flange 76" can be tipped upwardly and will clear a leg 104 of the T-bar component 40 shown on the right side in FIG. 11. The entire air treatment unit 10" can then be shifted to the right in FIG. 11 so that the flange 76" bridges, and is supported cooperatively by, the legs 98, 104.

The wires 82 can be electrically connected at the junction box 88.

Figure 13:
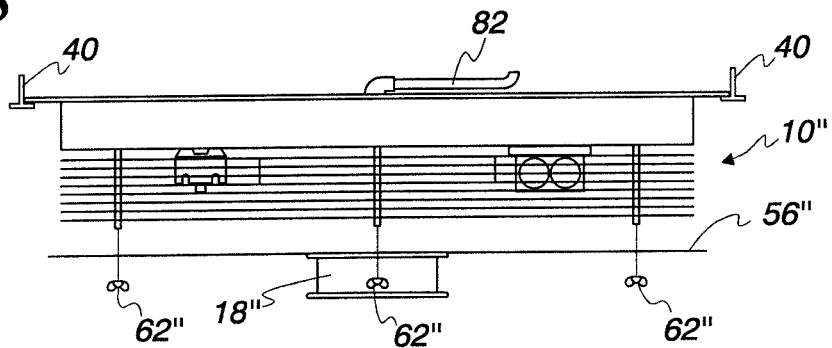
FIG. 13 is a view as in FIG. 12 with a bottom wall of the air treatment unit separated.

By separating the wingnuts 62", the bottom wall 56" and air moving assembly/fan 18" can be lowered as a unit, as shown in FIG. 13, to assist assembly, maintenance, cleaning, etc.

The bottom wall 56" can then be re-secured to assume the FIG. 14 state.

Figure 15:
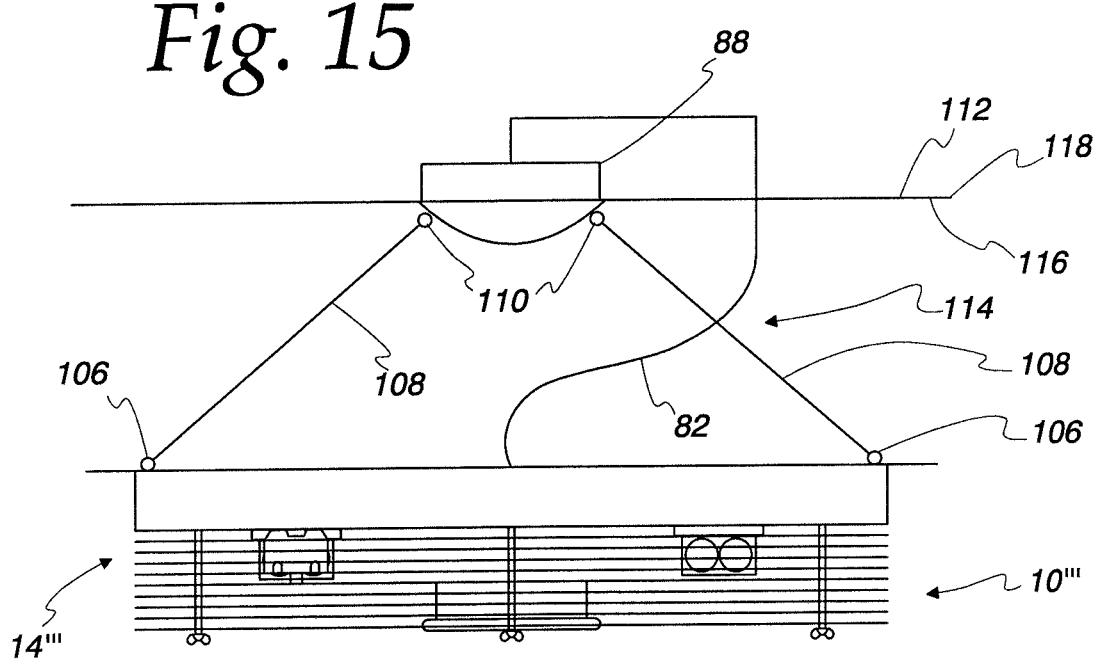
FIG. 15 is a side elevation view of a still further modified form of air treatment unit suspended in an operative state from a ceiling.

In FIG. 15, an air treatment unit is shown at 10''' that is substantially the same as the air treatment unit 10' with the exception that the frame 14''' has a plurality of mounting eyelets 106 fixed thereto. The eyelets 106 accommodate cables 108 which connect between the eyelets 106 and separate eyelets 110 fixed to a wall 112 at which the frame 14''' is operatively positioned. The eyelets 106, 110 and cables 108 cooperatively make up a suspension assembly at 114 through which the frame 14''' is spaced from a downwardly facing surface 116 on a wall 118 with the frame 14''' operatively positioned.

Of course, virtually any type of a conventional structure might be used to make up the suspension assembly to establish the relationship between the air treatment unit 10''' and the associated wall 118.

Wires 82 can be extended from the frame 14''' to the junction box 88 to electrically connect operating components.

With all embodiments, the main frame portions and subframe portions may be configured to define spaces for electrical components and wiring needed to power the lamps, air moving assemblies, etc. It is not necessary to get into all of the details of the electrical components and their connection, as one skilled in the art would be able to readily devise different component arrangements to achieve the objectives set forth herein.

As noted above, the inventive air treatment unit can be used to replace a supply vent conventionally used to distribute air in an occupied space. Alternatively, a more passive interaction between the air treatment unit and an existing duct outlet is effected.

The air treatment unit can be operated to disinfect with air movement induced through the duct 24 and/or by the air moving assembly 18. That is, the forced air source 26 and air moving assembly 18 may be separately operated or operated together, in the latter case causing a synergistic effect.

The foregoing disclosure of specific embodiments is intended to be illustrative of the broad concepts comprehended by the invention.

The invention claimed is:

1. An air treatment unit comprising:
   a frame;
   a source of UV light that is configured to disinfect air,
   the frame configured to be mounted in an operative position within a space in which air is to be disinfected,
   the frame configured to allow air in the space to be directed in a manner that the air is caused to be disinfected by UV light from the source of UV light with the frame and source of UV light each operatively positioned; and
   an air moving assembly that causes air within the space to be directed into a volume that has UV light rays from the source of UV light therein capable of disinfecting air,
   wherein the air treatment unit is configured to define a primary treatment volume, the primary treatment volume bounded by a bottom wall making up a part of the frame,
   wherein the frame further comprises an air guidance assembly that extends substantially fully around an axis extending through the primary treatment volume,
   wherein the air guidance assembly is configured to define at least one elongate opening through which disinfected air is communicated from the primary treatment volume in a pattern substantially fully around the axis to outside of the frame and the air treatment unit in a radial direction within a region of the space outside of the primary treatment volume with the frame operatively positioned and the air moving assembly operated.

2. The air treatment unit according to claim 1 wherein an air guidance assembly extends around the axis and is configured to define radial communication paths for air between the primary treatment volume and a region of the space outside of the primary treatment volume substantially fully around the axis.

3. The air treatment unit according to claim 1 wherein the air guidance assembly comprises a plurality of spaced slats and the at least one elongate opening comprises a louver between at least first and second of the spaced slats.

4. The air treatment unit according to claim 1 wherein the air moving assembly comprises a fan on the frame that is configured to draw air in the space upwardly into the primary treatment volume with the frame operatively positioned.

5. The air treatment unit according to claim 4 wherein the source of UV light comprises a plurality of lamps at spaced angular positions around the axis.

6. The air treatment unit according to claim 4 wherein with the frame operatively positioned the fan causes air within the space to move in a substantially vertically directed path into the primary treatment volume.

7. The air treatment unit according to claim 6 wherein the axis extends through the vertically directed path in which air is moved by the fan.

8. The air treatment unit according to claim 7 wherein the frame is symmetric on diametrically opposite sides of a reference plane containing the axis.

9. The air treatment unit according to claim 1 wherein the frame is configured to be flush mounted to a downwardly facing ceiling surface with the frame operatively positioned.

10. The air treatment unit according to claim 1 wherein the frame comprises at least one support edge configured to engage a ceiling grid T-bar system so as to thereby maintain the frame in the operative position.

11. The air treatment unit according to claim 1 further comprising a suspension assembly configured to maintain the frame spaced from a downwardly facing ceiling surface with the frame operatively positioned.

12. The air treatment unit according to claim 1 in combination with a support for the frame relative to which the frame is maintained in the operative position and further in combination with a duct through which air is forced into the space, wherein the duct is configured to cause air expelled from the duct to be moved directly into the primary treatment volume.

13. An air treatment unit comprising:
   a frame;
   a source of UV light that is configured to disinfect air,
   the frame configured to be mounted in an operative position within a space in which air is to be disinfected,
   the frame configured to allow air from a duct through which air is forced into the space to be directed in a manner that expelled air from the duct is caused to be disinfected by UV light from the source of UV light with the frame and source of UV light each operatively positioned; and
   an air moving assembly that causes air within the space to be directed into a volume that has UV light rays from the source of UV light therein capable of disinfecting air,
   the air treatment unit provided in combination with a support for the frame relative to which the frame is maintained in the operative position and further in combination with a duct through which air is forced into the space, wherein the frame is configured to define a primary treatment volume and the duct is configured to cause air expelled from the duct to be moved directly into the primary treatment volume, wherein the air from the duct moves in a downwardly directed path into the primary treatment volume, wherein the air moving assembly comprises a fan configured to draw air in the space in an upwardly directed path into the primary treatment volume.

14. The air treatment unit according to claim 13 wherein the upwardly and downwardly directed paths at least partially coincide so that air in the upwardly and downwardly directed paths is caused to mix, wherein the frame has at least one elongate opening situated so that a volume of the mixed air is diverted in a non-vertical direction through the at least one elongate opening from the primary treatment volume into a region of the space outside of the primary treatment volume.

15. The air treatment unit according to claim 14 wherein the primary treatment volume has a vertically extending central axis with the frame operatively positioned, the central axis extending through and generally parallel to the upwardly and downwardly directed paths, and the source of UV light comprises a plurality of lamps spaced from the central axis and from each other around the central axis.

16. The air treatment unit according to claim 15 wherein the plurality of UV lamps are arranged around the central axis to produce a substantially uniform density of UV light rays within the primary treatment volume.

17. An air treatment unit comprising:

a frame;

a source of UV light that is configured to disinfect air, the frame configured to be mounted in an operative position within a space in which air is to be disinfected, the frame configured to allow air in the space to be directed in a manner that the air is caused to be disinfected by UV light from the source of UV light with the frame and source of UV light each operatively positioned; and an air moving assembly that causes air within the space to be directed into a volume that has UV light rays from the source of UV light therein capable of disinfecting air, wherein the air treatment unit is configured to define a primary treatment volume through which an axis extends, the frame further comprising an air guidance assembly that extends around the axis and is configured so that air disinfected by the source of UV light is directed from the primary treatment volume to outside of the frame and the air treatment unit guidingly in a radial flow pattern substantially fully around the axis as the air moving assembly is operated.

18. The air treatment unit according to claim 17 wherein the air guidance assembly comprises first and second substantially flat slats with a volume therebetween through which disinfected air is guided radially outwardly in the flow pattern, the first and second slats residing in substantially parallel planes that are substantially orthogonal to the axis.

* * * * *

EX PARTE REEXAMINATION CERTIFICATE (12084th)
United States Patent
Skelton

(10) Number: US 10,753,626 C1
(45) Certificate Issued: *Jul. 1, 2022

(54) AIR TREATMENT UNIT

(71) Applicant: PetAirapy LLC, St. Charles, IL (US)

(72) Inventor: David Skelton, Bartlett, TN (US)

(73) Assignee: PetAirapy LLC

Reexamination Request:
No. 90/014,918, Dec. 7, 2021

Reexamination Certificate for:
Patent No.: 10,753,626
Issued: Aug. 25, 2020
Appl. No.: 15/871,719
Filed: Jan. 15, 2018

( * ) Notice: This patent is subject to a terminal disclaimer.

(51) Int. Cl.
| F24F 3/16 | (2021.01) |
| A61L 9/20 | (2006.01) |
| F24F 8/22 | (2021.01) |

(52) U.S. Cl.
CPC ............... *F24F 3/16* (2013.01); *A61L 9/20* (2013.01); *A61L 2209/12* (2013.01); *A61L 2209/134* (2013.01); *A61L 2209/16* (2013.01); *F24F 8/22* (2021.01)

(58) Field of Classification Search
None
See application file for complete search history.

(56) References Cited

To view the complete listing of prior art documents cited during the proceeding for Reexamination Control Number 90/014,918, please refer to the USPTO's public Patent Application Information Retrieval (PAIR) system under the Display References tab.

*Primary Examiner* — Krisanne M Jastrzab

(57) ABSTRACT

An air treatment unit has: a) a frame; b) a source of UV light that is configured to disinfect air, the frame configured to be mounted in an operative position within a space in which air is to be disinfected, the frame configured to allow air from a duct through which air is forced into the space to be directed in a manner that expelled air from the duct is caused to be disinfected by UV light from the source of UV light with the frame and source of UV light each operatively positioned; and c) an air moving assembly that causes air within the space to be directed into a volume that has UV light rays from the source of UV light therein capable of disinfecting air.

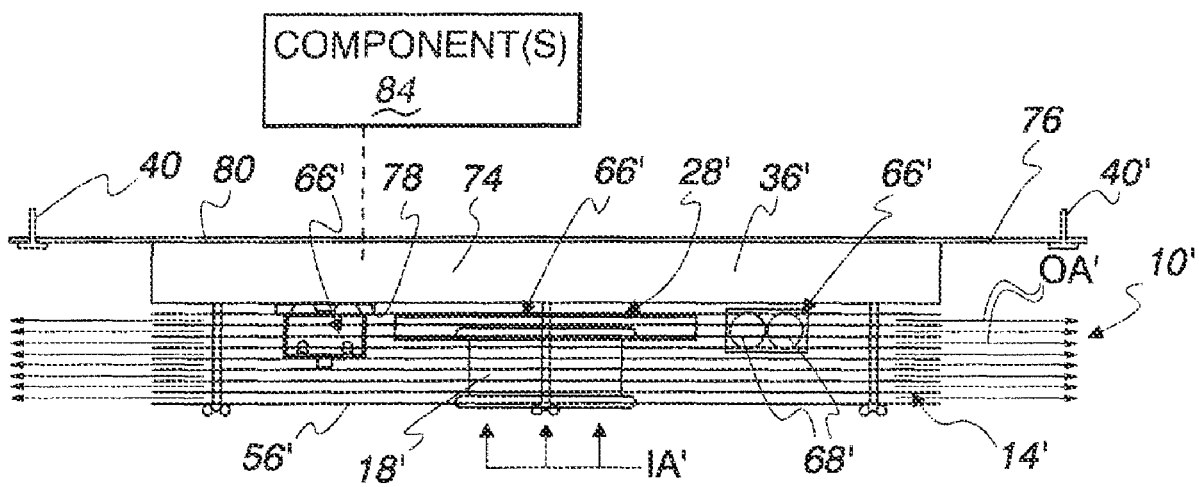

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-18 is confirmed.

\* \* \* \* \*